(12) United States Patent
Charles (10) Patent No.: US 10,463,533 B2
(45) Date of Patent: *Nov. 5, 2019

(54) INFUSION PRESSURE CONTROL USING BLOOD PRESSURE

(71) Applicant: Novartis AG, Basel (CH)

(72) Inventor: Steven T. Charles, Memphis, TN (US)

(73) Assignee: Novartis AG, Basel (CH)

( * ) Notice: Subject to any disclaimer, the term of this patent is extended or adjusted under 35 U.S.C. 154(b) by 887 days.

This patent is subject to a terminal disclaimer.

(21) Appl. No.: 14/293,613

(22) Filed: Jun. 2, 2014

(65) Prior Publication Data

US 2014/0276558 A1  Sep. 18, 2014

Related U.S. Application Data

(63) Continuation of application No. 13/112,504, filed on May 20, 2011, now Pat. No. 8,905,930.

(60) Provisional application No. 61/346,746, filed on May 20, 2010.

(51) Int. Cl.
| | |
|---|---|
| *A61B 3/16* | (2006.01) |
| *A61B 5/00* | (2006.01) |
| *A61M 35/00* | (2006.01) |
| *A61F 9/007* | (2006.01) |
| *A61M 5/172* | (2006.01) |

(52) U.S. Cl.
CPC .......... *A61F 9/00736* (2013.01); *A61F 9/007* (2013.01); *A61F 9/00781* (2013.01); *A61M 5/1723* (2013.01); *A61M 2005/1726* (2013.01); *A61M 2230/30* (2013.01)

(58) Field of Classification Search
CPC .. A61F 9/007; A61F 9/00736; A61F 9/00781; A61M 2005/1726; A61M 2230/30; A61M 5/1723

See application file for complete search history.

(56) References Cited

U.S. PATENT DOCUMENTS

| | | | |
|---|---|---|---|
| 3,929,124 | A | 12/1975 | Yablonski et al. |
| 4,007,742 | A | 2/1977 | Banko |
| 5,047,009 | A | 9/1991 | Morris et al. |
| 6,110,110 | A | 8/2000 | Dublin et al. |
| 2010/0145302 | A1 | 6/2010 | Cull et al. |
| 2011/0087086 | A1 | 4/2011 | Falck et al. |

*Primary Examiner* — Rebecca E Eisenberg (57) ABSTRACT

Methods, systems, and software for controlling infusion pressure, such as during a medical procedure, using systemic blood pressure are described. Systemic blood pressure, such as brachial arm blood pressure or radial artery blood pressure, may be used to estimate central retinal artery blood pressure to estimate critical closing pressure. Further, the disclosure relates to controlling infusion pressure to prevent an increase in intraocular pressure above the estimated critical closing pressure when such is not desired, and, when such is desired, using systemic blood pressure and infusion pressure to control an intentional increase in intraocular pressure above the estimated critical closing pressure to stop intraocular bleeding.

6 Claims, 5 Drawing Sheets

INFUSION PRESSURE CONTROL USING BLOOD PRESSURE

RELATED APPLICATIONS

This application is a continuation application of prior application Ser. No. 13/112,504, filed May 20, 2011, and claims the benefit of U.S. Provisional Application No. 61/346746, filed on May 20, 2010, the contents of all being incorporated herein by reference.

TECHNICAL FIELD

The present disclosure relates to controlling fluid infusion pressure, such as during an intraocular surgical procedure, utilizing systemic blood pressure. Particularly, the present disclosure describes systems and methods for controlling, and in some instances preventing interruption of, blood flow through the central retinal artery using both systemic blood pressure and fluid infusion pressure.

BACKGROUND

Low systemic blood pressure may be routine when operating on children and often occurs with adults undergoing general anesthesia or deep sedation. Intraocular pressure levels produced by an infusion system, such as during vitreoretinal surgery, may result in occlusion of the central retinal artery if the blood pressure is low. Prolonged vascular occlusion can result in blindness. Such procedures may involve a vitreous hemorrhage, a dense cataract, or some other obstruction that may prevent a medical practitioner from being able to observe circulation in the retinal vessels. Therefore, the retinal vessels are not visible and cannot be monitored for effective blood flow.

SUMMARY

According to one aspect, the disclosure describes a method for controlling infusion pressure, such as during an intraocular surgical procedure. The method may include determining an infusion pressure of a patient's eye with a first pressure determining device, determining a blood pressure indicative of a patient's central retinal artery blood pressure with a second pressure determining device, and determining, with a processor, an estimated critical closing pressure of the central retinal artery of the eye based on the systemic blood pressure.

Another aspect encompasses a computer program product for controlling an infusion pressure. The computer program product may include machine-readable instructions embodied on tangible media and operable when executed to read an infusion pressure of a patient's eye, determine an estimate of a patient's central retinal artery blood pressure, and determine an estimated critical closing pressure of the central retinal artery of the eye based on the estimated central retinal artery blood pressure.

A further aspect relates to a system for controlling infusion pressure during an intraocular surgical procedure. The system may include a data receival unit adapted to receive systemic blood pressure and infusion pressure. The system may also include a computational unit adapted to determine an estimated retinal artery blood pressure based on the received systemic blood pressure and determine an estimated critical closing pressure based on the estimated retinal artery blood pressure. The system may additionally include a logic unit adapted to compare infusion pressure with the estimated critical closure pressure and trigger an alarm when the infusion pressure reaches a selected pressure relative to the estimated critical closing pressure.

Another aspect relates to a computer-implemented method for controlling infusion pressure performed by a processor. The method may include determining an infusion pressure of a patient's eye, determining an estimate of a patient's central retinal artery blood pressure, and determining an estimated critical closing pressure of a central retinal artery of the eye based on the estimated central retinal artery blood pressure.

Another aspect relates to a system including memory for storing at least one of systemic blood pressure data, estimated central retinal artery blood pressure data, infusion pressure data, and estimated critical closing pressure data and one or more processors. The one or more processors may be operable to determine an infusion pressure of a patient's eye, determine an estimate of a patient's central retinal artery blood pressure, and determine an estimated critical closing pressure of a central retinal artery of the eye based on the estimated central retinal artery blood pressure.

The various aspects may include one or more of the following features. A blood pressure indicative of a patient's central retinal artery blood pressure may be determined by determining a patient's systemic blood pressure with a pressure determining device and converting the systemic blood pressure into the estimated central retinal artery blood pressure with a processor. Determining the patient's systemic blood pressure may include determining at least one of the patient's brachial artery blood pressure or radial artery blood pressure with a pressure determining device. The systemic blood pressure may be converted into the estimated central retinal artery blood pressure with an ophthalmodynamometry offset with a processor. The infusion pressure may be compared to the estimated critical closing pressure with a processor. An alarm may be triggered when the infusion pressure reaches a selected pressure relative to the estimated critical closing pressure. An alarm may be at least one of a visual or audible alarm. A patient's systemic blood pressure may be at least one of the patient's brachial artery blood pressure or radial artery blood pressure. Infusion pressure may be increased above the estimated critical closing pressure with a fluid flow device to stop intraocular bleeding. The infusion pressure may be increased above the estimated critical closing pressure for a selected period of time to stop intraocular bleeding at a site of the eye. A procedure may be performed at the site of the eye to prevent continued bleeding after lowering of the infusion pressure below the estimated critical closing pressure. Infusion pressure may be automatically adjusted when the infusion pressure is at a selected value relative to the estimated critical closing pressure. For example, infusion pressure may be reduced when the infusion pressure is equal to or greater than the estimated critical closing pressure.

The various aspects may also include one or more of the following features. Machine-readable instructions operable when executed to read a patient's systemic blood pressure may include machine-readable instructions operable when executed to read at least one of the patient's brachial artery blood pressure or radial artery blood pressure. Machine-readable instructions operable when executed to determine an estimate of a patient's central retinal artery blood pressure may include machine-readable instructions operable when executed to read a patient's systemic blood pressure and convert the systemic blood pressure into the estimated central retinal artery blood pressure. Machine-readable instructions operable when executed to convert the systemic blood pressure into the estimated central retinal artery blood pressure may include machine-readable instructions operable when executed to convert the systemic blood pressure into the estimated central retinal artery blood pressure with an ophthalmodynamometry offset. Machine-readable instructions may also be included that, when executed, trigger an alarm when the infusion pressure reaches a selected pressure relative to the estimated critical closing pressure. The machine-readable instructions operable when executed to trigger an alarm when the infusion pressure reaches a selected pressure relative to the estimated critical closing pressure may include machine-readable instructions operable when executed to trigger at least one of a visual or audible alarm. The machine readable instruction may be operable when to automatically adjusted infusion pressure when the infusion pressure is at a selected value relative to the estimated critical closing pressure. For example, infusion pressure may be reduced when the infusion pressure is equal to or greater than the estimated critical closing pressure.

The various aspects may further include one or more of the following features. A data receival unit adapted to receive systemic blood pressure may be adapted to receive at least one of brachial artery blood pressure or radial artery blood pressure. A computational unit adapted to determine an estimated retinal artery blood pressure based on the received systemic blood pressure may be adapted to convert the systemic blood pressure into the estimated retinal artery blood pressure using an ophthalmodynamometry offset. A logic unit adapted to trigger an alarm when the infusion pressure reaches a selected pressure relative to the estimated critical closing pressure may be adapted to trigger at least one of a visual or audible alarm.

The various aspects may also include one or more of the following features. An estimate of a patient's central retinal artery blood pressure may be determined by determining a patient's systemic blood pressure and converting the systemic blood pressure into the estimated central retinal artery blood pressure. The systemic blood pressure may be converted into the estimated central retinal artery blood pressure with an ophthalmodynamometry offset. An alarm may be triggered when the infusion pressure reaches a selected pressure relative to the estimated critical closing pressure. Triggering an alarm when the infusion pressure reaches a selected pressure relative to the estimated critical closing pressure may include triggering at least one of a visual or audible alarm. A patient's systemic blood pressure may be determined by determining at least one of the patient's brachial artery blood pressure or radial artery blood pressure. The infusion pressure may be increased above the estimated critical closing pressure to stop intraocular bleeding. Increasing the infusion pressure above the estimated critical closing pressure to stop intraocular bleeding may include increasing the infusion pressure above the estimated critical closing pressure for a selected period of time to stop intraocular bleeding at a site of the eye and performing a procedure, during application of the increased infusion pressure, at the site of the eye to prevent continued bleeding after lowering of the infusion pressure below the estimated critical closing pressure. Infusion pressure may be automatically adjusted when the infusion pressure is at a selected value relative to the estimated critical closing pressure. For example, the infusion pressure may be reduced when the infusion pressure is equal to or greater than the estimated critical closing pressure.

The various aspects may include one or more of the following features. One or more processors operable to determine an estimate of a patient's central retinal artery blood pressure may include one or more processors operable to receive a patient's systemic blood pressure and convert the systemic blood pressure into the estimated central retinal artery blood pressure. One or more processors operable to convert the systemic blood pressure into the estimated central retinal artery blood pressure may include one or more processors operable to convert the systemic blood pressure into the estimated central retinal artery blood pressure with an ophthalmodynamometry offset. The one or more processors may be further operable to trigger an alarm when the infusion pressure reaches a selected pressure relative to the estimated critical closing pressure. The triggered alarm may be at least one of a visual or audible alarm. One or more processors operable to receive a patient's systemic blood pressure may include one or more processors operable to receive at least one of the patient's brachial artery blood pressure or radial artery blood pressure. One or more processors may be further operable to automatically adjust infusion pressure when the infusion pressure is at a selected value relative to the estimated critical closing pressure. the one or more processors is further operable to automatically adjust infusion pressure when the infusion pressure is at a selected value relative to the estimated critical closing pressure comprises one or more processors operable to automatically reduce infusion pressure when the infusion pressure is equal to or greater than the estimated critical closing pressure.

The details of one or more implementations of the present disclosure are set forth in the accompanying drawings and the description below. Other features, objects, and advantages will be apparent from the description and drawings, and from the claims.

DETAILED DISCLOSURE

The present disclosure describes methods, systems, and computer software for controlling fluid infusion pressure (i.e., the pressure at which fluid is infused into an eye during an intraocular surgical procedure) (hereinafter referred to as "infusion pressure") using systemic blood pressure. For example, surgical procedures on an eye may include aspiration of a portion of vitreous humor (interchangeably referred to as "vitreous material") from the posterior segment as well as infusion of a fluid into the eye, such as artificial aqueous humor or other fluid (collectively referred to as "infusion fluid"). Aspirating vitreous humor from and infusing infusion fluid into the eye may cause a change in the intraocular pressure ("IOP"). IOP may be particularly affected by the infusion pressure. For example, infusion pressure may be representative of IOP when little or no aspiration from the eye is occurring. However, infusion pressure may be used as an adequate representative of IOP under other conditions during intraocular surgical procedures. The present disclosure describes methods and systems for controlling infusion pressure and, thereby, controlling IOP, during medical procedures as well as providing notification to a medical services provider that infusion pressure has reached a selected pressure.

In an example implementation, an infusion pressure application for controlling infusion pressure ("infusion services") is described. In some instances, the infusion pressure application may be implemented via a system (interchangeably referred to as an "ocular system") that is at least partially electronically implemented. For example, the ocular system may be incorporated into one or more devices. In some instances, the ocular system may form part of a medical apparatus, such as an intraocular medical apparatus. Further, the ocular system may be at least partially implemented over a computer network to one or more remote devices. The present disclosure also describes computer networks that may be utilized for implementing the infusion services in some implementations.

Figure 1:
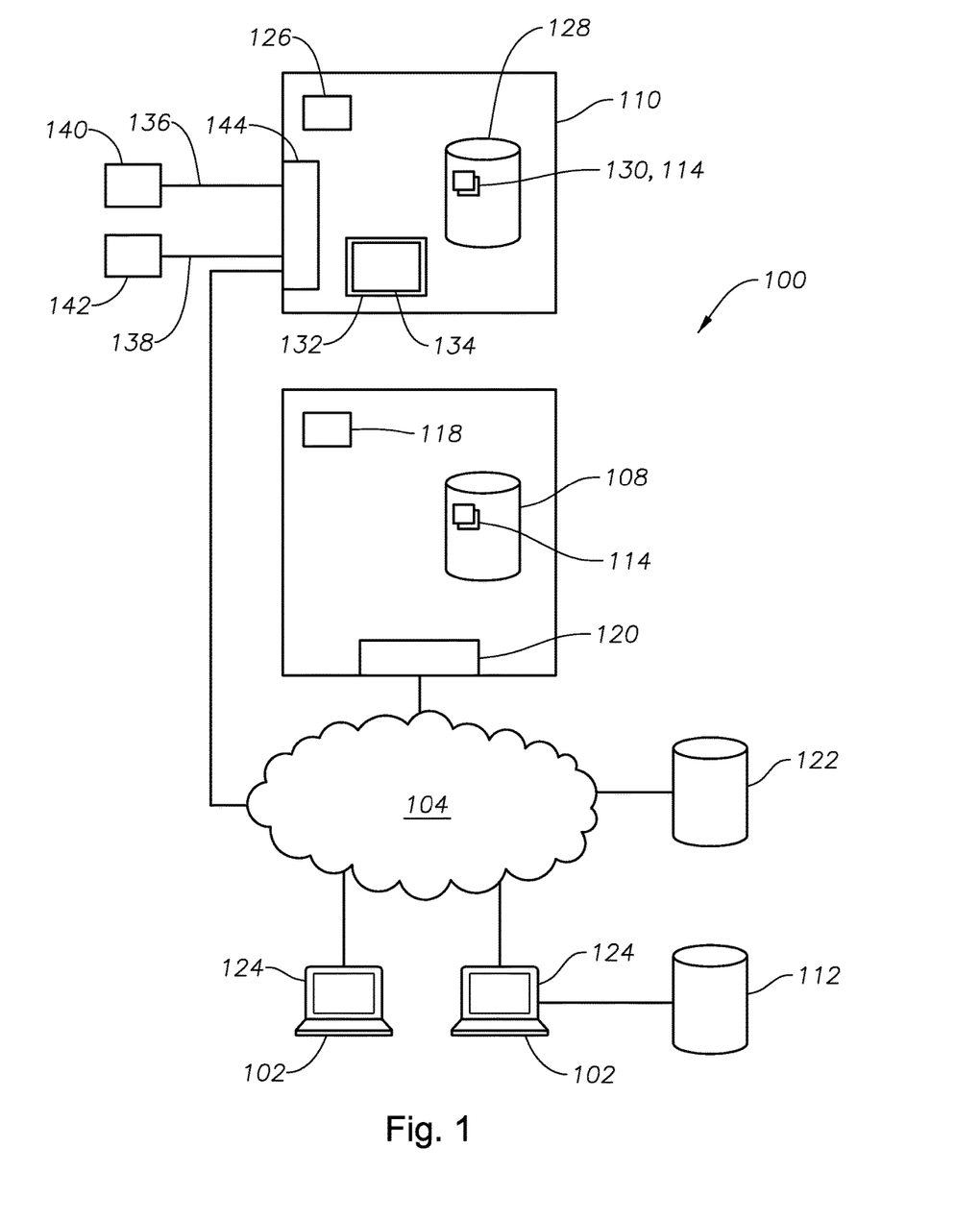
FIGS. 1-3 are example systems for controlling fluid infusion pressure into an eye.

FIG. 1 illustrates an example system 100 for dynamically implementing the infusion services. System 100 may encompass an example ocular system that may be operable to transmit information to one or more clients 102, receive information from one or more of the clients 102, and otherwise administer and control various aspects of the infusion services.

System 100 may be a distributed client/server system that spans one or more networks, such as network 104. In such implementations, data may be communicated or stored in an encrypted format using any standard or proprietary encryption algorithm. In other instances, the data may be stored at least partially in an unencrypted format. System 100 may be in a dedicated environment, implemented across a local area network or subnet, or implemented in any other suitable environment without departing from the scope of this disclosure. In some instances, the system 100 may include or be communicably coupled with a server 106, one or more clients 102, network 104, and one or more medical devices 110. Additionally, one or more of the clients 102 may be communicably coupled to a repository 112. In some implementations, the one or more clients 102 may be consoles utilized by medical practitioners to control the infusion services, either alone or in addition to other aspects associated with the system 100. Further, system 100 may include additional or different features and components than those described.

Server 106 may include an electronic computing device operable to receive, transmit, process, and store data associated with system 100. Generally, FIG. 1 provides merely one example of computers that may be used with the disclosure. Each computer is generally intended to encompass any suitable processing device. For example, although FIG. 1 illustrates one server 106 that may be used with the disclosure, system 100 can be implemented using computers other than servers, as well as a server pool. Indeed, server 106 may be any computer or processing device such as, for example, a blade server, general-purpose personal computer (PC), Macintosh, workstation, Unix-based computer, or any other suitable device. In other words, the present disclosure contemplates computers other than general purpose computers as well as computers without conventional operating systems. Server 106 may be adapted to execute any operating system including Linux, UNIX, Windows Server, or any other suitable operating system. According to one embodiment, server 106 may also include or be communicably coupled with a web server and/or a mail server.

The server 106 may include local memory 108. Memory 108 may include any memory or database module and may take the form of volatile or non-volatile memory including, without limitation, magnetic media, optical media, random access memory (RAM), read-only memory (ROM), removable media, or any other suitable local or remote memory component. Illustrated memory 108 may include, among other items, an infusion pressure application 114. For example, medical practitioners may use the clients 102 to interact with activities associated with operation of the medical device 110, including the infusion services at least partially provided by the infusion pressure application 114. For example, in some instances, the infusion services may be conducted entirely on the server 102 with information sent to and from each client 104 and/or medical device 110 to interact with the infusion pressure application 114.

In other instances, infusion services of the infusion pressure application 114 may be performed partially on the server 106 and partially at one or more locations remote from the server 106. For example, in some implementations, the infusion services of the infusion pressure application 114 may be partially or fully performed on the medical device 110.

Memory 108 may store classes, frameworks, applications, backup data, jobs, or other information that includes any parameters, variables, algorithms, instructions, rules, or references thereto. Memory 108 may also include other types of data, such as environment and/or application description data, application data for one or more applications, as well as data involving virtual private network (VPN) applications or services, firewall policies, a security or access log, print or other reporting files, HyperText Markup Language (HTML) files or templates, related or unrelated software applications or sub-systems, and others. Consequently, memory 108 may also be considered a repository of data, such as a local data repository from one or more applications. Memory 108 may also include data that can be utilized by the infusion pressure application 114.

Server 106 may also include processor 118. Processor 118 executes instructions and manipulates data to perform the operations of the server 106, e.g., computational and logic operations, and may be, for example, a central processing unit (CPU), a blade, an application specific integrated circuit (ASIC), or a field-programmable gate array (FPGA). Although FIG. 1 illustrates a single processor 118 in server 106, multiple processors 118 may be used according to particular needs and reference to processor 118 is meant to include multiple processors 118 where applicable. In the illustrated embodiment, processor 118 executes infusion pressure application 114.

Server 106 may also include interface 120 for communicating with other computer systems, such as clients 102, over network 104 in a client-server or other distributed environment. For example, the interface 120 may receive data from different parts of the system 100 or from sources outside of the system 100 as well as transmit data to different parts of the system 100 or to locations outside of the system 100. In certain embodiments, server 106 receives data from internal or external senders through interface 120 for storage in memory 108 and/or processing by processor 118. Generally, interface 120 comprises logic encoded in software and/or hardware in a suitable combination and operable to communicate with network 104. More specifically, interface 120 may comprise software supporting one or more communications protocols associated with communications network 104 or hardware operable to communicate physical signals.

Network 104 facilitates wireless or wireline communication between computer server 106 and any other local or remote computer, such as clients 102. Network 104 may be all or a portion of an enterprise or secured network. In another example, network 104 may be a VPN merely between server 106 and client 102 across wireline or wireless link. Such an example wireless link may be via 802.11a, 802.11b, 802.11g, 802.20, WiMax, and many others. While illustrated as a single or continuous network, network 104 may be logically divided into various sub-nets or virtual networks without departing from the scope of this disclosure, so long as at least a portion of network 104 may facilitate communications among server 106, at least one client 102, and other device, such as medical device 110, discussed in more detail below. For example, server 106 may be communicably coupled to a repository 122 through one sub-net while communicably coupled to a particular client 102 through another. In other words, network 104 encompasses any internal or external network, networks, sub-network, or combination thereof operable to facilitate communications between various computing components in system 100. Network 104 may communicate, for example, Internet Protocol (IP) packets, Frame Relay frames, Asynchronous Transfer Mode (ATM) cells, voice, video, data, and other suitable information between network addresses (collectively or interchangeably referred to as "information"). Network 112 may include one or more local area networks (LANs), radio access networks (RANs), metropolitan area networks (MANs), wide area networks (WANs), all or a portion of the global computer network known as the Internet, and/or any other communication system or systems at one or more locations. In certain embodiments, network 104 may be a secure network accessible to users via certain local or remote clients 102.

Client 102 may be any computing device operable to connect or communicate with server 106 or network 104 using any communication link. At a high level, each client 102 includes or executes at least graphical user interface ("GUI") or application interface (collectively referred to as "GUI 124") and comprises an electronic computing device operable to receive, transmit, process, and store any appropriate data associated with system 100. It will be understood that there may be any number of clients 102 communicably coupled to server 104. Further, "client 102" and "user" may be used interchangeably as appropriate without departing from the scope of this disclosure. Moreover, for ease of illustration, each client 104 is described in terms of being used by one user. But this disclosure contemplates that many users may use one computer or that one user may use multiple computers. As used in this disclosure, client 102 is intended to encompass a personal computer, touch screen terminal, workstation, network computer, kiosk, wireless data port, smart phone, personal data assistant (PDA), one or more processors within these or other devices, or any other suitable processing device. For example, client 102 may be a PDA operable to wirelessly connect with an external or unsecured network. In another example, client 102 may comprise a laptop computer that includes an input device, such as a keypad, touch screen, mouse, or other device that can accept information, and an output device that conveys information associated with the operation of server 106 or clients 102, including digital data, visual information, or user interface, such as GUI 124. Both input devices and output devices may include fixed or removable storage media such as a magnetic computer disk, CD-ROM, or other suitable media to both receive input from and provide output to users of clients 102 through, for example, a display. In some instances, the display may include the client portion of GUIs 124.

GUI 124 may include a graphical user interface operable to allow the user of client 102 to interface with at least a portion of system 100 for any suitable purpose, such as viewing application or other transaction information. For example, GUI 124 could provide information associated with a medical procedure, including detailed information related to infusion pressure and/or other information related to the infusion pressure application 114. Generally, GUI 124 may provide a particular user with an efficient and user-friendly presentation of information provided by or communicated within system 100. GUI 124 may include a plurality of customizable frames or views having interactive fields, pull-down lists, and buttons operated by the user. GUI 124 may also present a plurality of portals or dashboards. For example, GUI 124 may display a secure webpage that allows users to input and define parameters associated with the infusion services. It should be understood that the term graphical user interface may be used in the singular or in the plural to describe one or more graphical user interfaces and each of the displays of a particular graphical user interface. Indeed, reference to GUI 124 may indicate a reference to the front-end or a component of infusion pressure application 114, as well as the particular interface accessible via client 102, as appropriate, without departing from the scope of this disclosure. Therefore, GUI 124 contemplates any graphical user interface. For example, in some instances, the GUI 124may include a generic web browser or touch screen that processes information in system 100 and efficiently presents the results to the user. In other instances, the GUI 124 may include a custom or customizable interface for displaying and/or interacting with the various features of the infusion pressure application 114 or other infusion services. Further, in some instances, server 106 may accept data from client 102 and return the appropriate HTML or XML responses to the browser using network 104. In some instances, information between the server and the client 102 may be transmitted via a web browser (e.g., Microsoft Internet Explorer or Netscape Navigator) or other application. In some instances, software utilized for transmitted information may be integrated within the infusion pressure application 114.

The medical device 110 may include a processor 126, similar to processor 118, memory 128, similar to memory 108, and one or more applications 130. For example, the one or more applications 130 may include infusion pressure application 114 or a portion thereof. Further, the medical device 110 may be adapted to execute any suitable operating system. The medical device 110 may also include a display 132 for displaying information to a user, such as a medical practitioner. Further, the display 132 may present the present information to the user via a GUI 134, which may be similar to the GUI 124, described above. The medical device 110 may send and receive information to and from the server 106 as well as to and from clients 102 via the network 104. Aspects of operation of the medical device 110 may be monitored and/or controlled from the medical device 110, the server 106, and/or the client 102. For example, one or more aspects or services of operation of the medical device 110 may be performed and/or altered by the medical device 110, by the server 106, and/or by a user via client 124.

The medical device 110 may also include an interface 144, similar to interface 120, for communicating data with components, both within and outside of the system, including computer systems, such as clients 102, server 106, or other components, directly or over network 104 in a client-server or other distributed environment. The medical device 110 may receive one or more inputs, such as inputs 136 and 138. Inputs 136 and 138, as well as any other desired inputs to the medical device 110, may be received and/or outputs transmitted via the interface 144.

In some instances, the inputs 136 and 138 may respectively represent infusion services information, such as measurement data representative of a medical condition or aspect of a patient's health. Inputs 136 and 138 may be communicated to the medical device 110 in any desirable manner. For example, one or more of the inputs 136, 138 may be transmitted to the medical device 110 over a wireline connection (e.g., via an Ethernet, USB, IEEE 1394, or other wired connection) or wireless connection (e.g., an 802.11a, 802.11b, 802.11g, 802.20, WiMax, ZigBee, Ultra-Wideband ("UWB"), or any other wireless link).

In some implementations, input 136 may represent systemic blood pressure data, while input 138 may represent data indicative of intraocular pressure, such as infusion pressure data. However, inputs may represent any characteristics of a patient's health, such as heart rate, pulse, respiration rate, etc. Further, inputs 136 and 138 may be provided to the medical device 110 from components 140 and 142, respectively. Further, in some instances, input 136 and input 138 may be in the form of a digital or analog signal. Components 140 and 142 may be another device, such as another medical device, from which data may be desired. In some instances components 140 and/or 142 may be a sensor coupled directly or indirectly to the patient. Example devices 140 and 142 may be anesthesia devices or sensors, vital sign monitoring devices or sensors, or any other desired device or sensor that may provide information associated with performing a medical procedure on a patient. In some instances, devices 140 and 142 may be adapted to determine one or more of a patience's vital signs, such as blood pressure, pulse rate, etc. For example, device 140 and/or 142 may be adapted to determine blood pressure by sensing blood pressure.

In still other implementations, medical device 110 may incorporate devices and/or sensors 140 and 142. For example, medical device 110 may include pressure measurement components, temperature measurement components, flow rate measurement components, as well as others. In some instances, the pressure measurement component may include a pressure transducer, or, in other instances, the pressure measurement component may include a combination of devices and/or sensors adapted to measure pressure, such as one or more pressure transducers, one or more flow rate measurement devices, one or more temperature sensors, and/or any other suitable instrument. Further, medical device 110 may include any other or different sensors and devices than those described.

Figure 2:
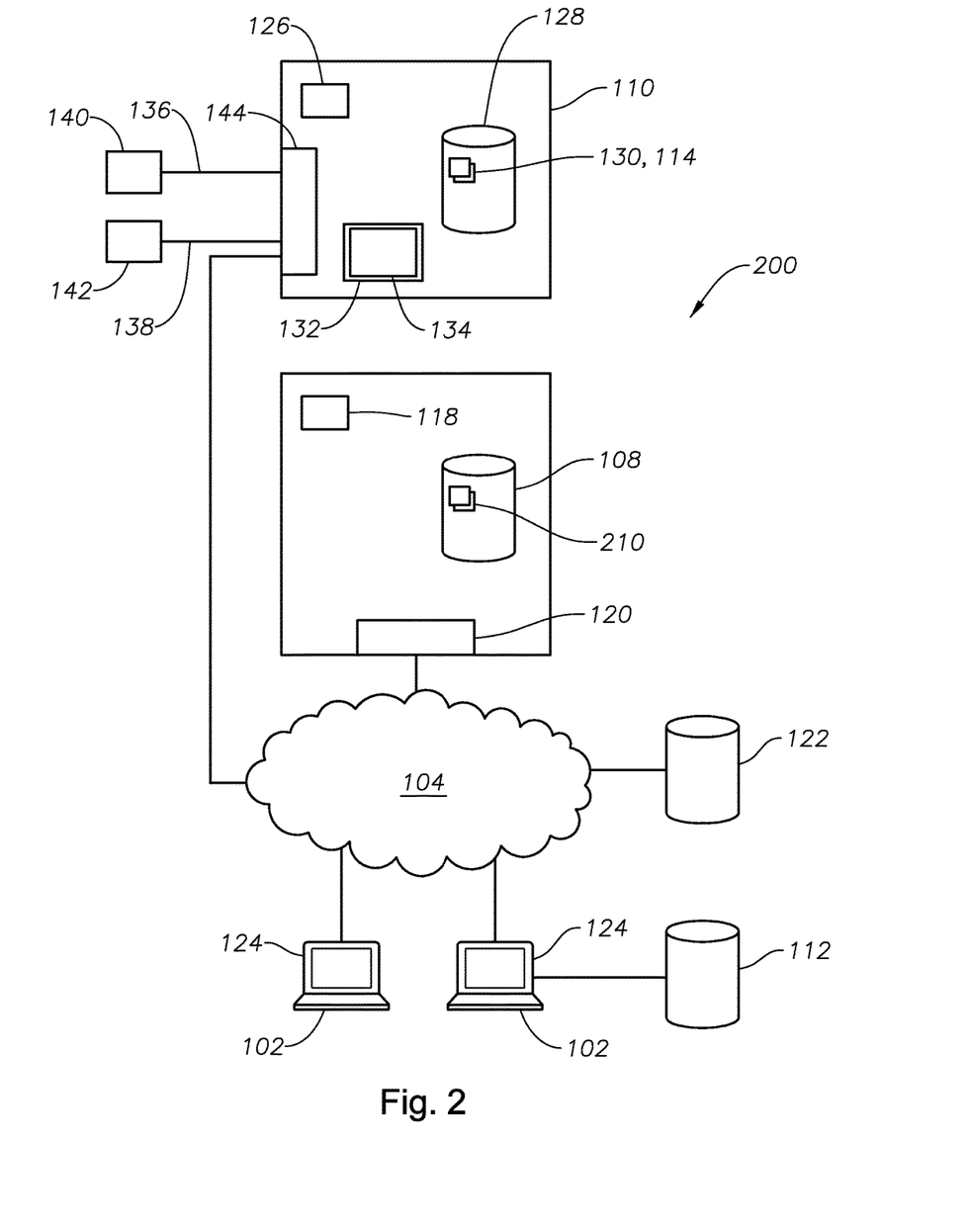

While the above description with respect to FIG. 1 describes the server 106 at least partially executing and/or providing services associated with the infusion pressure application 114, FIG. 2 illustrates an alternate implementation in which services associated with infusion pressure application 114 may entirely be performed on and/or by the medical device 110. Further, the medical device 110 may also perform other functions or provide other services.

Accordingly, FIG. 2 shows a system 200 including medical device 110, server 106, network 104, and clients 102, similar to those described above. The server 106 may include one or more application 210 provided in memory 108. Also similar to above, the medical device 110 may receive inputs 136 and 138. Other components may also be included in system 200. For example, system 200 may include multiple medical devices and/or multiple servers. Communication between the medical device 110 and client 102 may be provided via network 104.

Figure 3:
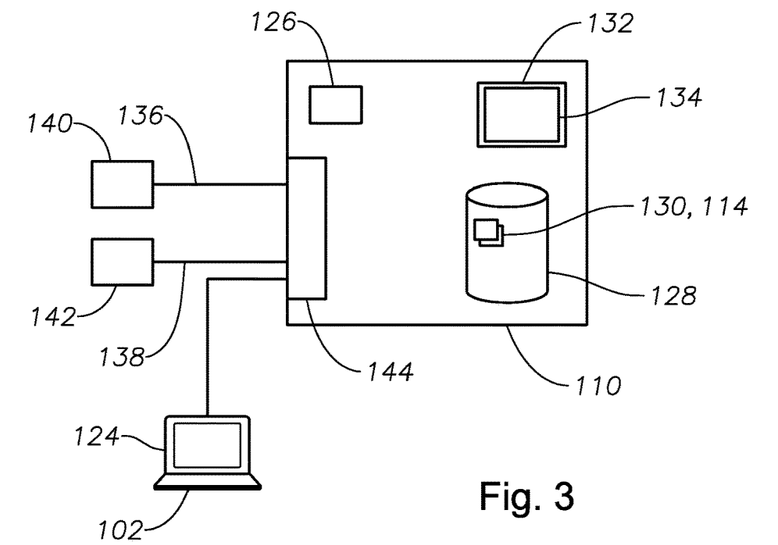

FIG. 3 shows a still further implementation in which the medical device 110 for performing the services associated with the infusion pressure application 114 is in a stand-alone configuration. The medical device 110 may be similar to that described above. For example, the medical device 110 may include, among other features, processor 126, memory 128, display 132, and receive inputs 136 and 138. These components may be similar to those components described above. The memory 128 may include infusion pressure application 114, and processor 126 may execute the instructions of infusion pressure application 114. Accordingly, the medical device 110 may exclusively provide all services associated with the infusion pressure application 114. The medical device 110 may also be coupled to a client 102, through which a user may monitor or make changes to an operating condition of the medical device 110.

In some implementations, the medical device 110 may be a vitreoretinal surgical system. Example vitreoretinal surgical systems may include, but are not limited to, the Accurus® Surgical System produced by Alcon Laboratories, Inc. of Alcon Laboratories, Inc., 6201 South Freeway, Fort Worth, Tex. 76134 and the Constellation® Vision System also produced by Alcon Laboratories, Inc.

Figure 4:
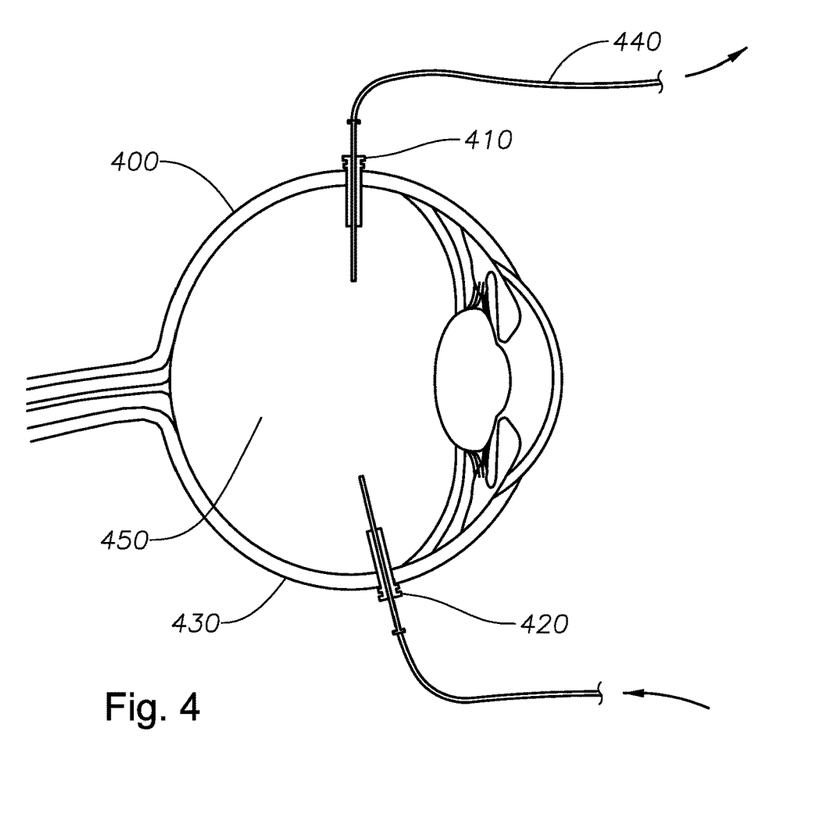
FIG. 4 is a cross sectional view of an eye undergoing an intraocular surgical procedure.

The infusion pressure application 114 may provide one or more of the features described below. FIG. 4 shows a cross-sectional view of an eye 400 undergoing a medical procedure involving, for example, a vitrectomy. A first cannula 410 and a second cannula 420 may be inserted through the sclera 430 and into the posterior segment 40 of the eye 20. Vitreous material may be evacuated through the cannula 410 and carried away through a tube 440 or other suitable structure. Infusion fluids may be introduced into the posterior segment 450 via the second cannula 420.

As the vitreous material is removed from and infusion fluid is introduced into the posterior segment 450, intraocular pressure may fluctuate. For example, if the rate of aspiration of material from the eye is greater than the rate material is infused into the eye, the IOP may drop. On the other hand, if the rate at which material is aspirated from the eye is less than the rate at which material is infused into the eye, the IOP may increase. Generally, infusion pressure may be determined and used as a proxy for IOP. That is, during an intraocular surgical procedure, infusion pressure generally may have the greatest effect on and, therefore, be representative of IOP. A signal corresponding to the infusion pressure may be transmitted to a processor, such as processor 126 or 118.

The infusion pressure may be carefully controlled. For example, if infusion pressure exceeds a certain threshold, IOP corresponding thereto may exceed the critical closing pressure ("CCP"). Consequently, vascular occlusion may result. During a surgical procedure, IOP may be altered, for example, by adjusting the infusion pressure. In other instances, IOP may be altered by adjusting the rate at which vitreous material is aspirated, the rate at which infusion fluid is infused, or both.

CCP may vary with a patient's blood pressure. For example, for a patient having a low blood pressure or as a patient's blood pressure drops during a medical procedure, the pressure necessary to prevent blood flow through the central retinal artery (i.e., the CCP) will be lower. On the other hand, for a patient with high blood pressure or as the patient's blood pressure increases during a medical procedure, the CCP raises.

In some implementations, during an intraocular surgical procedure, such as one involving a vitrectomy, a patient's systemic blood pressure may be monitored. In some instances, the measured systemic blood pressure may be brachial artery blood pressure. The systemic blood pressure may be monitored and provided as an input to a control or monitoring device. The systemic blood pressure may be measured, for example, by a pressure cuff or other suitable device, and a signal corresponding thereto may be transmitted to a processor, such as the processor that receives the intraocular blood pressure. Alternately, a signal corresponding to the systemic blood pressure may be transmitted to a different processor.

The systemic blood pressure may be converted into an estimated central retinal artery blood pressure (interchangeably referred to as "retinal blood pressure") according to known methods. For example, an offset, such as a conversion factor or algorithm, for converting from systemic blood pressure to retinal blood pressure may be an ophthalmodynamometry derived offset. That is, the offset may be obtained from ophthalmodynamometry studies. A processor may determine the retinal blood pressure using the systemic blood pressure and offset. Accordingly, the processor may determine an estimated critical closing pressure and compare the estimated CCP to the infusion pressure.

In some instances, if the infusion pressure is equal to or above the retinal blood pressure or another selected pressure, the infusion pressure may be automatically adjusted to prevent occlusion from occurring. Alternately or in addition, an alarm may be triggered by the infusion pressure condition. For example, in some instances, a medical device, such as medical device 110, may receive as inputs infusion pressure and systemic blood pressure, automatically determine an estimated retinal blood pressure from the received systemic blood pressure, determine the estimated critical closure pressure from the retinal blood pressure, and compare the infusion pressure to a selected pressure (e.g., the estimated critical closing pressure or another pressure associated therewith). If the infusion pressure is equal to, above, or at some other level relative to the selected pressure, the medical device may automatically adjust the infusion pressure to keep the infusion pressure at a desired level. Further, the medical device may also trigger an alarm to notify the medical practitioners of the infusion pressure level.

Infusion pressure may be increased or otherwise altered by adjusting a pressure head, such as by altering a pump speed, altering a gas pressure (such as in gas forced infusion or vented gas force infusion), or altering a gravity pressure head. A gravity pressure head may be altered by adjusting a height of a volume of fluid, such as by changing a height of a container of fluid either manually or in an automated fashion. For example, a gravity pressure head may be altered in an automated fashion with an electronically controlled motorized staff that automatically adjusts a height of a fluid container coupled thereto to maintain a desired pressure head. Collectively, mechanisms for accomplishing these pressure heads, such as those described above, may be referred to as "fluid flow devices".

In other implementations, the infusion pressure (and, hence, the IOP) may be intentionally increased above the CCP. For example, the infusion pressure may be intentionally increased above the CCP to stop intraocular bleeding. The infusion pressure may be maintained at the elevated pressure so that intraocular bleeding may be corrected. Once the site at which intraocular bleeding has been corrected and the infusion pressure may be lowered to a level below critical closing pressure, the bleeding is prevented from reoccurring. Example procedures and mechanisms for repairing a bleed site may include coagulation, suturing, and cauterization. Thereafter, infusion pressure may be lowered below the CCP thereby permitting blood flow through the central retinal artery.

Figure 5:
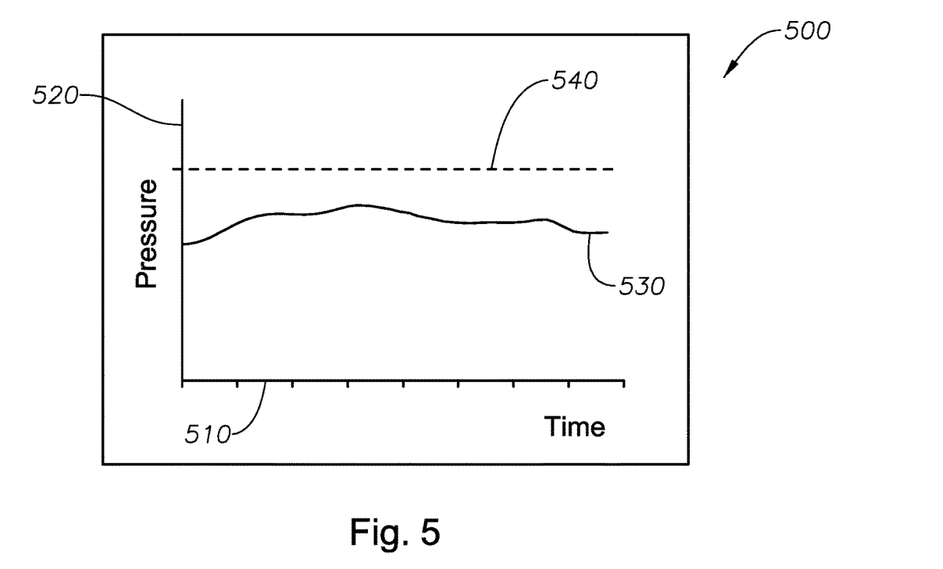
FIGS. 5-6 show example outputs of central retinal artery blood pressure and critical closing pressure.
Figure 6:
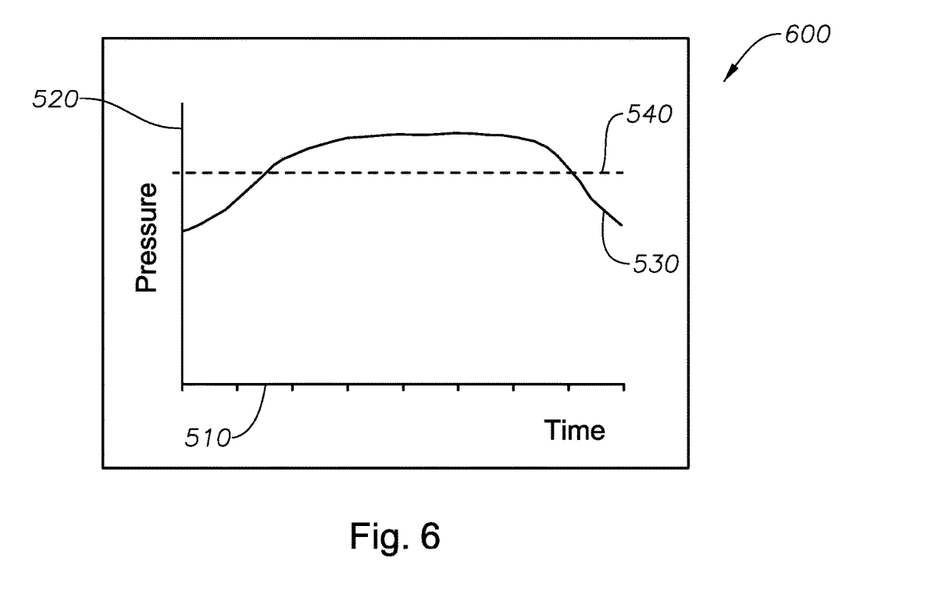

One or more of the systemic blood pressure, estimated retinal blood pressure, estimated CCP, or infusion pressure may be displayed to a user, such as a medical practitioner. For example, such output may be displayed on a display, such as display of a client 102 and/or display 132. The output may be incorporated into a GUI, such as GUI 124 and/or GUI 134. FIGS. 5-6 show example display outputs for presenting the outputted information to the user. FIG. 5 shows a display output 500 including a pair of axes 510, 520. In some instances, the horizontal axis 510 my represent "time", while the vertical axis 520 may indicate "pressure". FIG. 5 shows the behavior over time of infusion pressure 530 relative to estimated CCP 540. In this instance, the infusion pressure 530 is shown below the estimated CCP 540 for a period of time. FIG. 6 also shows an example display output 600 in which infusion pressure 530 has increased beyond the estimated CCP 540 for a period of time.

Figure 7:
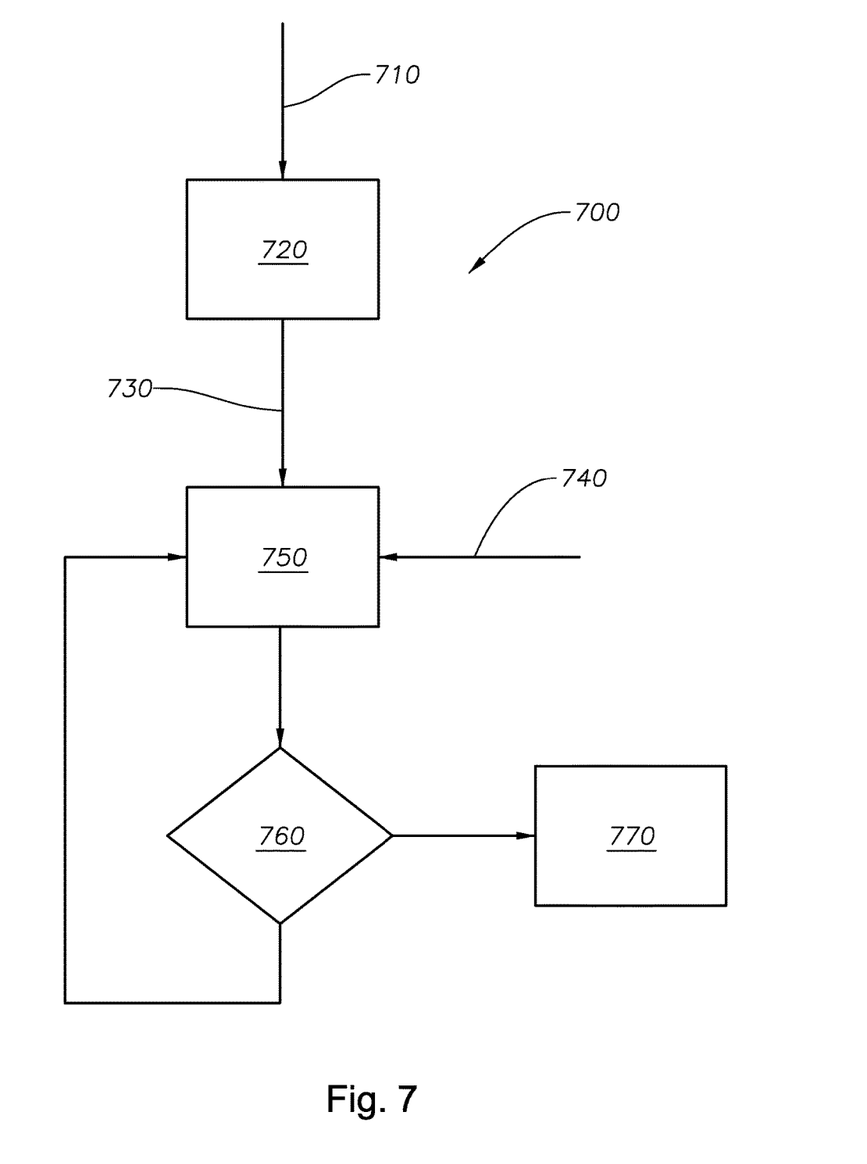
FIG. 7 is an example method for controlling fluid infusion pressure to which an eye is subjected during an intraocular surgical procedure.

FIG. 7 shows an example method 700 for controlling infusion pressure using systemic blood pressure. Systemic blood pressure 710 may be obtained and used as an input at 720. At 720, the systemic blood pressure 710 may be converted into retinal blood pressure 730. For example, the retinal blood pressure 730 may be determined from the systemic blood pressure 710 using an offset obtained from ophthalmodynamometry studies. The determined retinal blood pressure 730 may be defined as the critical closing pressure. At 750, the critical closing pressure may be compared to infusion pressure 740. At 760, if the infusion pressure 740 is greater than and/or equal to the critical closing pressure, an alarm 770 may be triggered. A return to 750 may be made at which time subsequent critical closing pressure and infusion pressure 750 comparisons may be made.

In some instances, the alarm may be a visual alarm. Example visual alarms may include a message displayed on a display, a flashing light, or some other visual indicator. In other instances, the alarm may be an audible alarm. Example audible alarms may include a buzzer, a siren, or some other audible cue to indicate to the user or medical practitioner that an alarm has been triggered. In still other instances, the audible alarm may be in the form of a pre-recorded or computer-generated message. For example the pre-recorded or computer-generated message may be or mimic a human voice that indicates that a pressure is above a predetermined value. The message may also repeat at regular, irregular, or any other desired interval and include recitation of an elapsed time during which the pressure has exceeded the predetermined pressure value. Further, the alarms may have an escalation feature. That is, alarm of one type may be triggered at a first pressure, while a second type of alarm may be triggered at a different pressure. Such a feature may provide for a series of escalating alarms as the measured infusion pressure increases above predetermined intervals.

It is noted that, in some instances, while an alarm may be triggered at 770 based on determinations made at 760 the method may be applied on a continuous basis whether or not an alarm has been triggered. Thus, the example method 500 may represent a continuous control method that, in some instances, may be a real-time control method. Consequently, the implementations of the methods described herein may be implemented into a control system that continuously intakes systemic blood pressure and infusion pressure as inputs and determine whether an alarm is to be triggered.

In some implementations, a medical device incorporating one or more of the features described herein, such as medical device 110, may include a feature that automatically adjusts the infusion pressure (such as by increasing the rate at which material is aspirated from the eye, the rate at which material is infused into the eye, or both) in the event the infusion pressure increases above or decreases below a selected value or, for example, if the rate of change of the infusion pressure leads to or is likely to an infusion pressure above critical closing pressure.

It should be understood that, although many aspects have been described herein, some implementations may include all of the features, while others may include some features while omitting others. That is, various implementations may include one, some, or all of the features described herein without departing from the scope of the disclosure. Further, additional features not described herein may also be included in the various implementations described herein without departing from the scope of the disclosure.

A number of implementations have been described. Nevertheless, it will be understood that various modifications may be made without departing from the spirit and scope of the disclosure. Accordingly, other implementations are within the scope of the following claims.

What is claimed is:

1. A method for controlling infusion pressure during an intraocular surgical procedure, the method comprising:
   determining an infusion pressure of a patient's eye with a first pressure determining device;
   determining a blood pressure indicative of a patient's central retinal artery blood pressure with a second pressure determining device;
   determining, with a processor, an estimated critical closing pressure of a central retinal artery of the eye based on the blood pressure indicative of a patient's central retinal artery blood pressure;
   comparing, with the processor, the infusion pressure to the estimated critical closing pressure; and
   triggering an alarm when the infusion pressure reaches a selected pressure relative to the estimated critical closing pressure.

2. The method of claim 1, wherein triggering an alarm when the infusion pressure reaches a selected pressure relative to the estimated critical closing pressure comprises triggering at least one of a visual or audible alarm.

3. The method of claim 1, further comprising automatically adjusting infusion pressure when the infusion pressure is at a selected value relative to the estimated critical closing pressure.

4. The method of claim 3, wherein automatically adjusting the infusion pressure when the infusion pressure is at a selected value relative to the estimated critical closing pressure comprises automatically reducing infusion pressure when the infusion pressure is equal to or greater than the selected pressure and wherein the selected pressure is the estimated critical closing pressure.

5. A method for controlling infusion pressure during an intraocular surgical procedure, the method comprising:
   determining an infusion pressure of a patient's eye with a first pressure determining device;
   determining a blood pressure indicative of a patient's central retinal artery blood pressure with a second pressure determining device;
   determining, with a processor, an estimated critical closing pressure of a central retinal artery of the eye based on the blood pressure indicative of a patient's central retinal artery blood pressure; and
   increasing the infusion pressure above the estimated critical closing pressure with a fluid flow device to stop intraocular bleeding.

6. The method of claim 5, wherein increasing the infusion pressure above the estimated critical closing pressure with a fluid flow device to stop the intraocular bleeding comprises:
   increasing the infusion pressure above the estimated critical closing pressure for a selected period of time to stop intraocular bleeding at a site of the eye; and
   performing, during application of the increased infusion pressure, a procedure at the site of the eye to prevent continued bleeding after lowering of the infusion pressure below the estimated critical closing pressure.

* * * * *